(12) United States Patent
Guerrier

(10) Patent No.: US 10,080,833 B2
(45) Date of Patent: Sep. 25, 2018

(54) DIALYSIS BED

(71) Applicant: Walker S. Guerrier, Baldwin, NY (US)

(72) Inventor: Walker S. Guerrier, Baldwin, NY (US)

(*) Notice: Subject to any disclaimer, the term of this patent is extended or adjusted under 35 U.S.C. 154(b) by 316 days.

(21) Appl. No.: 15/187,364

(22) Filed: Jun. 20, 2016

(65) Prior Publication Data
US 2016/0367423 A1    Dec. 22, 2016

Related U.S. Application Data

(60) Provisional application No. 62/181,312, filed on Jun. 18, 2015.

(51) Int. Cl.
| | |
|---|---|
| A61G 7/10 | (2006.01) |
| A61M 1/36 | (2006.01) |
| A61G 13/02 | (2006.01) |
| A61M 25/02 | (2006.01) |
| A61G 13/12 | (2006.01) |
| A61G 7/05 | (2006.01) |

(52) U.S. Cl.
CPC ........... *A61M 1/3661* (2014.02); *A61G 13/02* (2013.01); *A61M 25/02* (2013.01); *A61G 7/051* (2016.11); *A61G 7/0506* (2013.01); *A61G 13/1235* (2013.01)

(58) Field of Classification Search
CPC ........................................ A61G 7/10

USPC ................................ 5/81.1 R, 86.1, 81.1 HS
See application file for complete search history.

(56) References Cited

U.S. PATENT DOCUMENTS

| | | | | |
|---|---|---|---|---|
| 6,802,091 | B1 * | 10/2004 | Harris | A61G 7/1019 |
| | | | | 5/81.1 HS |
| 6,907,625 | B2 * | 6/2005 | Nomura | A61G 7/053 |
| | | | | 5/617 |
| 7,578,011 | B2 * | 8/2009 | Johnson | A61G 7/1019 |
| | | | | 5/81.1 C |

* cited by examiner

*Primary Examiner* — Fredrick C Conley
(74) *Attorney, Agent, or Firm* — Dunlap, Bennett & Ludwig, PLLC

(57) ABSTRACT

A dialysis bed and additional accessories are provided. The dialysis bed includes a head board, a foot board and a base. The head board includes a head board slot running from a side edge towards a central portion of the head board. The foot board includes a foot board slot running from a side edge towards a central portion of the foot board. The foot board slot aligns with the head board slot. The base connects the head board and the foot board together and is disposed beneath the slots. The present invention further includes a sliding platform. The sliding platform includes a first end having a first handle and a second end having a second handle. The first handle slidably engages within the head board slot and the second handle slidably engages within the foot board slot.

9 Claims, 8 Drawing Sheets

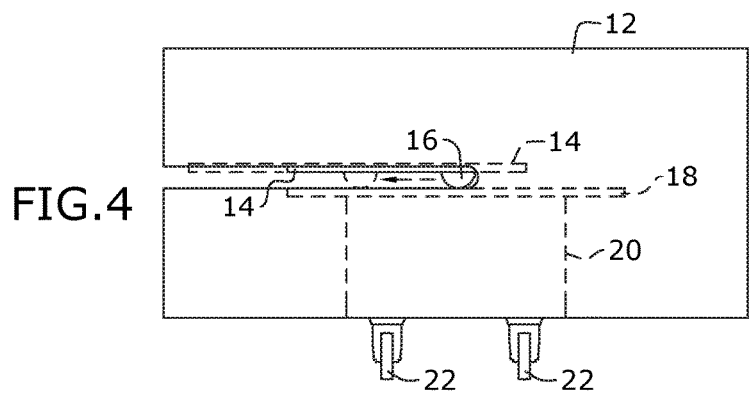
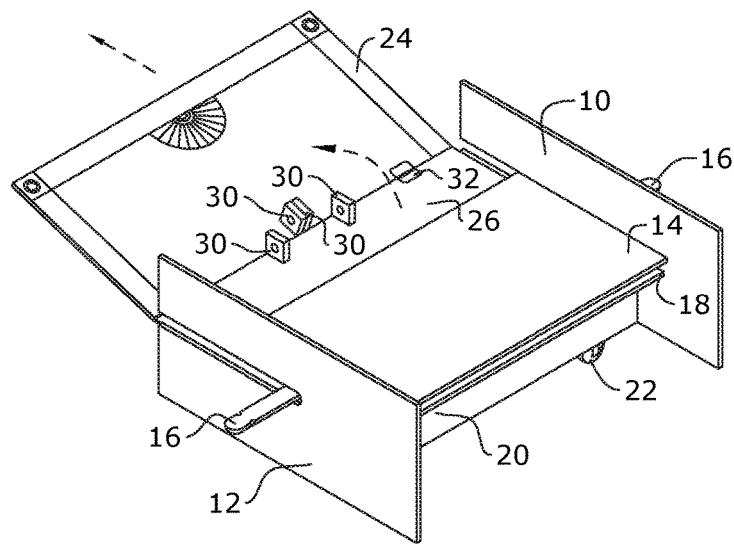
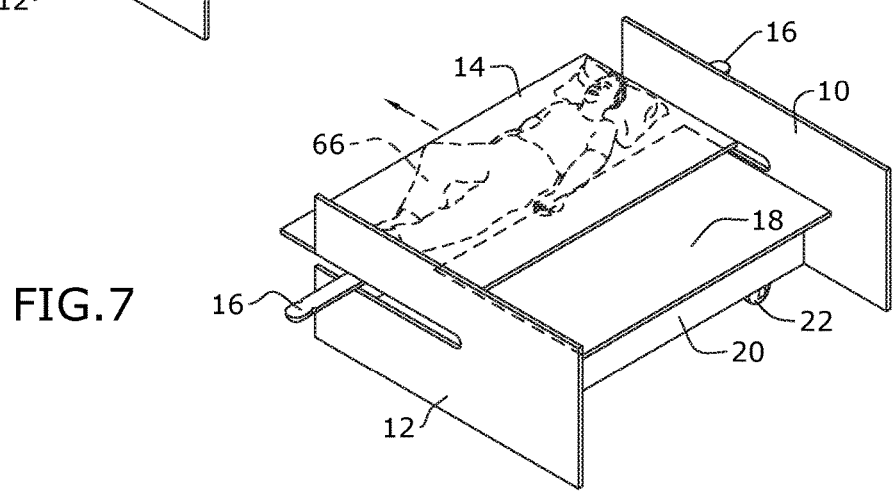

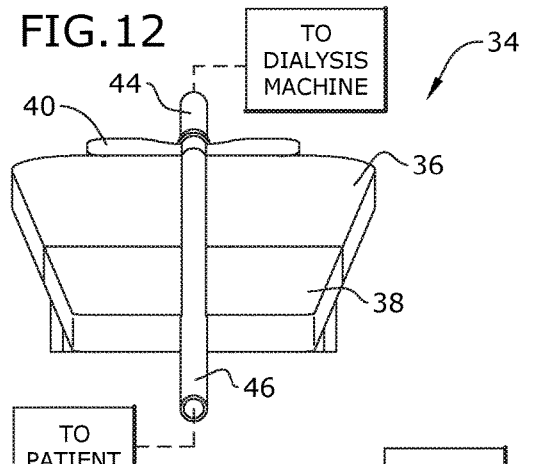
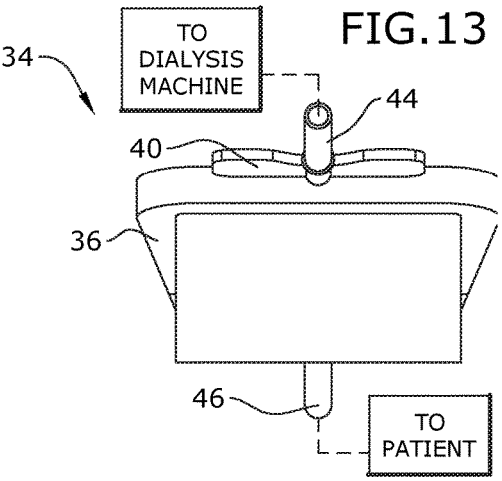
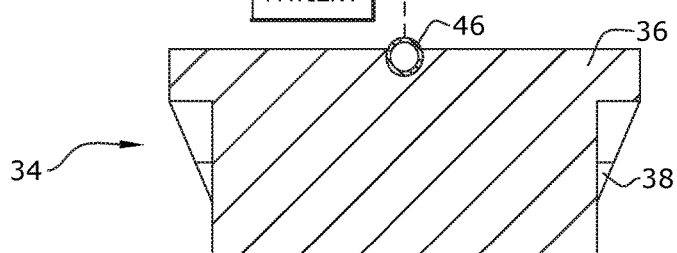
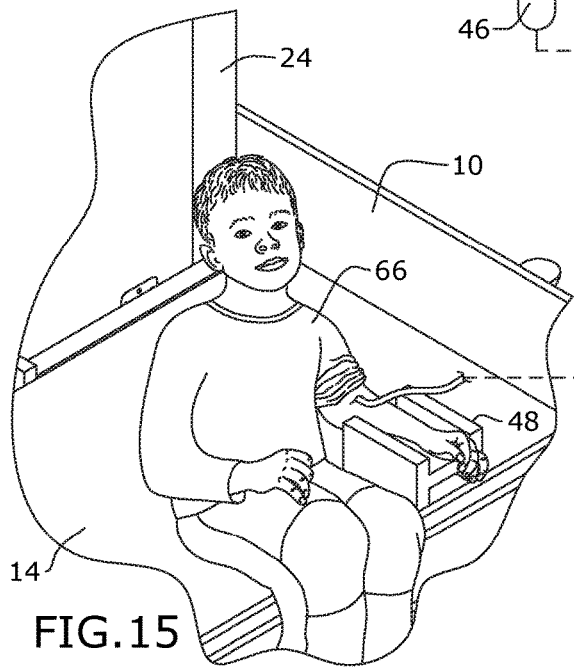
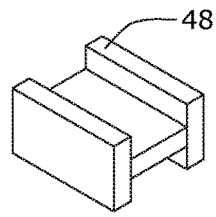

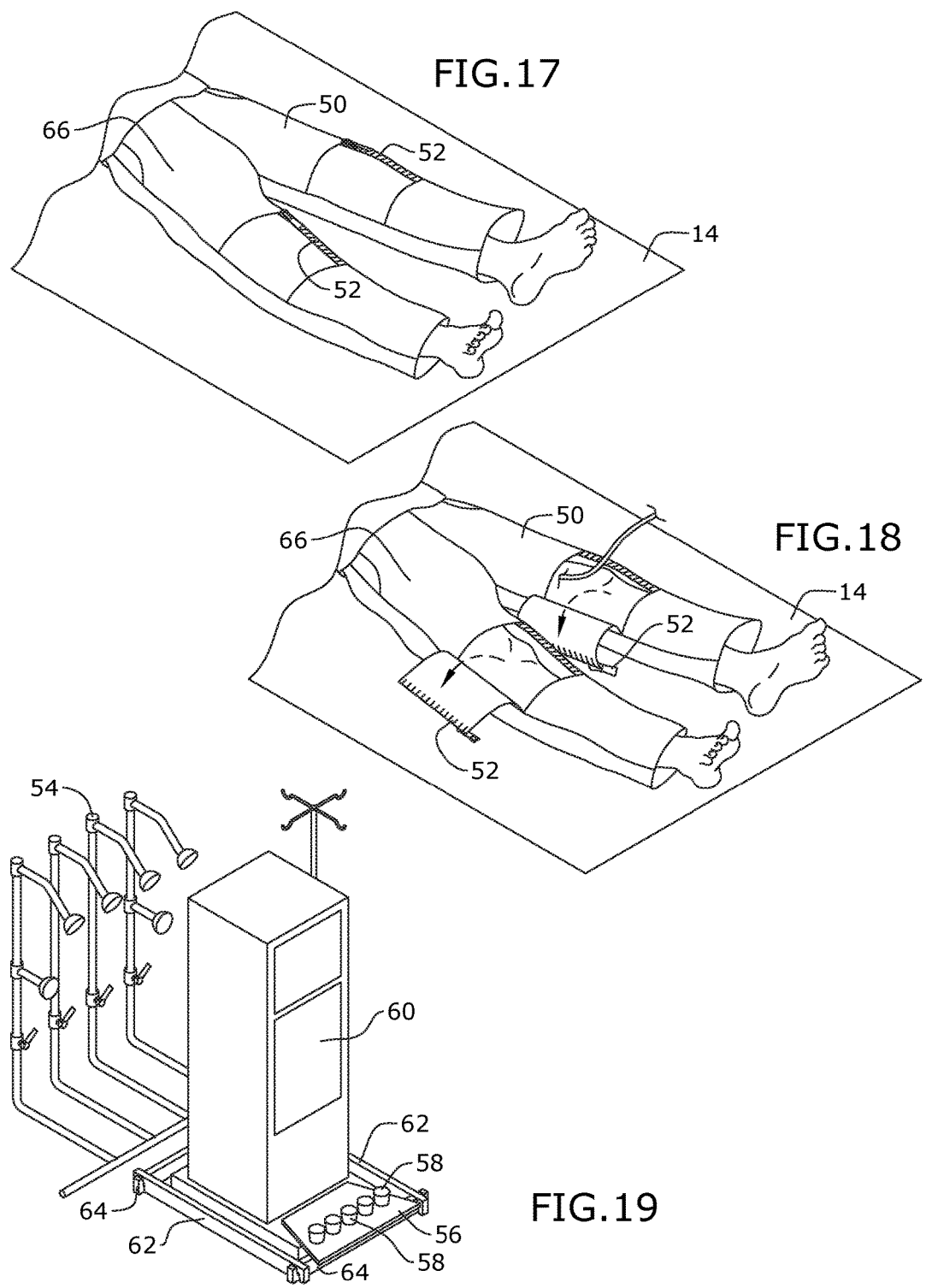

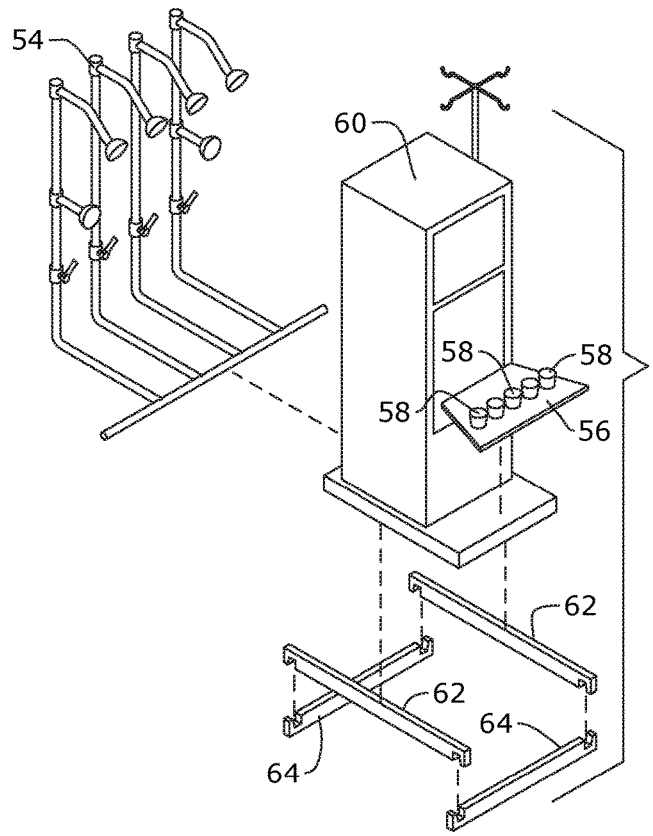
FIG.20
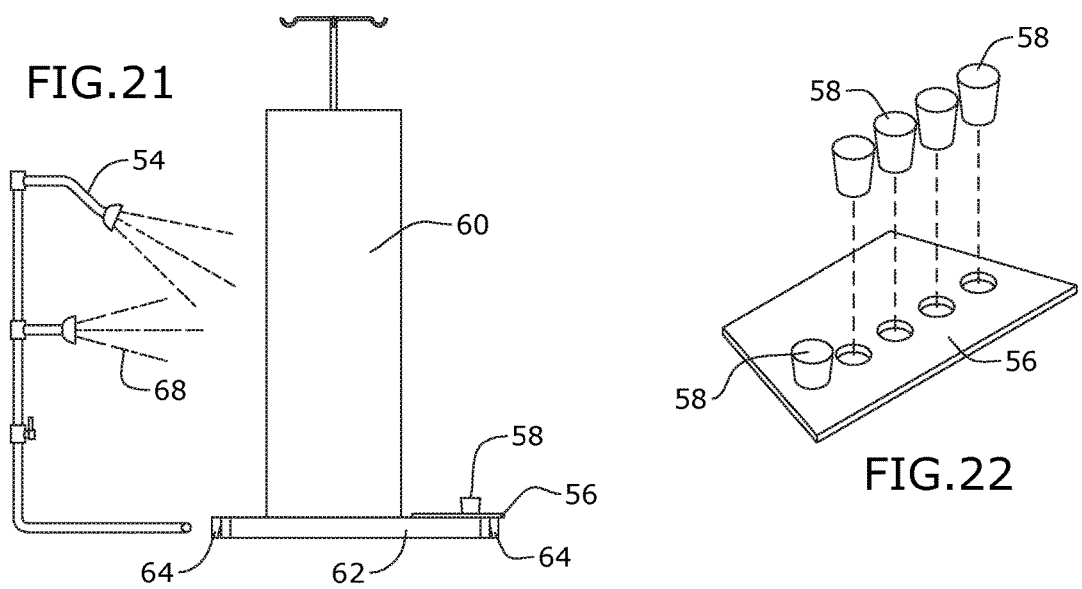
FIG.21
FIG.22

DIALYSIS BED

CROSS-REFERENCE TO RELATED APPLICATION

This application claims the benefit of priority of U.S. provisional application No. 62/181,312, filed Jun. 18, 2015, the contents of which are herein incorporated by reference.

BACKGROUND OF THE INVENTION

The present invention relates to dialysis and, more particularly, to a dialysis bed.

In medicine, dialysis is a process for removing waste and excess water from the blood, and is used primarily as an artificial replacement for lost kidney function in people with kidney failure. Dialysis may be used for those with an acute disturbance in kidney function (acute kidney injury, previously acute renal failure), or progressive but chronically worsening kidney function—a state known as chronic kidney disease stage 5 (previously chronic renal failure or end-stage renal disease). The latter form may develop over months or years, but in contrast to acute kidney injury is not usually reversible, and dialysis is regarded as a "holding measure" until a kidney transplant can be performed, or sometimes as the only supportive measure in those for whom a transplant would be inappropriate. Currently, regular beds are used for dialysis patients. Regular beds do not accommodate the needs of a dialysis patient.

As can be seen, there is a need for an improved dialysis bed that allows the patient to shift.

SUMMARY OF THE INVENTION

In one aspect of the present invention, a dialysis bed comprises: a head board comprising a head board slot running from a side edge towards a central portion of the head board; a foot board comprising a foot board slot running from a side edge towards a central portion of the foot board, wherein the foot board slot aligns with the head board slot; a base connecting the head board and the foot board together; and a sliding platform comprising a first end comprising a first handle and a second end comprising a second handle, wherein the first handle slidably engages within the head board slot and the second handle slidably engages within the foot board slot.

These and other features, aspects and advantages of the present invention will become better understood with reference to the following drawings, description and claims.

BRIEF DESCRIPTION OF THE DRAWINGS

FIG. 4 is a perspective view of the invention illustrating the hinge pin being removed;
FIG. 6 is a perspective view of the invention shown in use illustrating the active platform being moved (side panel and side panel base platform removed for clarity);
FIG. 7 is a side view of the invention illustrating the active platform being moved (side panel and side panel base platform removed for clarity);
FIG. 12 is a front view of the needle adjuster;
FIG. 13 is a rear view of the needle adjuster;
FIG. 14 is a section view of the needle adjuster taken from 14-14 in FIG. 8;
FIG. 15 is a perspective view of the arm rest shown in use;
FIG. 16 is a perspective view of the arm rest;
FIG. 17 is a perspective view of the pants illustrating the zipper closed;
FIG. 18 is a perspective view of the pants illustrating the zipper opened shown in use;
FIG. 19 is a perspective view of the cleaning system, the prescription tray and the tray supports shown in use;
FIG. 20 is an exploded view of the cleaning system, the prescription tray and the tray supports;
FIG. 21 is a side view of the cleaning system, the prescription tray and the tray supports shown in use;
FIG. 22 is an exploded view of the prescription tray.

DETAILED DESCRIPTION OF THE INVENTION

Figure 1:
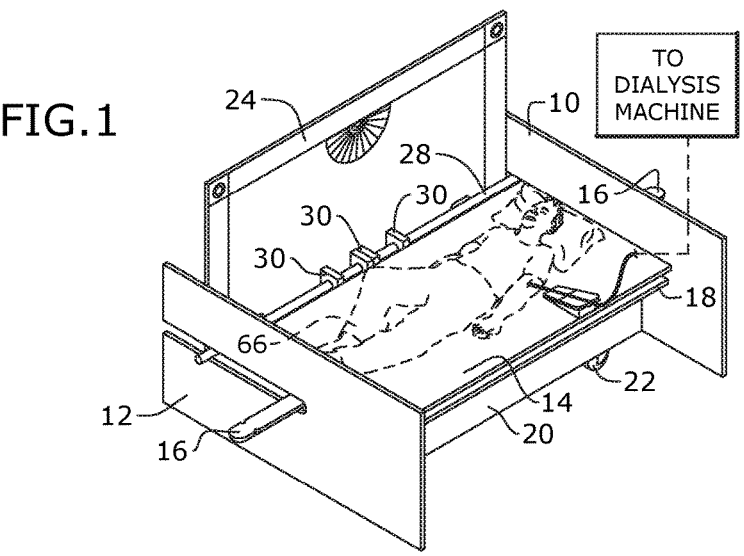
FIG. 1 is a perspective view of the invention shown in use.

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

The present invention includes a dialysis machine and its system components. The problem the present invention solves is it reduces repetitive injury, improves cost efficiency, and increases workers productivity. The present invention improves arterial flow, with a needle adjuster, reducing bleeding with blood reducer, and prevents patients from falling with a slide bed. Further, the bedding system rotates and thereby prevents injuries such as back and shoulder pain.

The lower part of the bed is called the semi rotation circle connecting the head bed. The purpose is to allow the core bed to rotate side by side. This rotation is what will allow the bed to move side to side allowing circulation to the body and the heart. This is how to reduce soars on the right side or left side of the human body. The core bed and its head part is the main rotating part. For the treatment of dialysis, connecting the patient to the dialysis machine allows a smooth dialysis treatment for patients who are doing 4 to 8 hours of dialysis treatment. The sliding part which is also the core bed with the assistance of trained medical staff which include Paramedics, Technicians, Nurses allowing the core bed to move up and slide to the right or left side. This is how to move the patient from the core bed to an ordinary bed, which will prevent medical staff from injuring their back.

With the aid of a power or manual jack the core bed lift up, (Dialysis) medical staff manually slides the bed to an ordinary bed. The dialysis set includes the following components: Head bed size; Head bed about 4 feet wide, length about 6 feet long, height about 42 inches. The space to the right or left side of the lower part of the head bed with semi circle is about 2 inches. The semi circle could be any circumference, such as the size of a penny, dime, nickel, quarter and the like.

The core bed may include a motor connecting to the core bed head, and rotates the bed side to side. The jack piece which is under the bed is used to lift up the bed automatically or manually. The main dialysis bed which could be made with woods, plastic, aluminum, copper, iron or the like, allows a dialysis patient to be able to enjoy an effective treatment. This bed would reduce cramping of the leg and abdominal region as well as neck, and solder discomfort.

To manufacture the bed, various tools and equipment may be used, such as screws, screw drivers, hand saw or electrical, hammer wrenches, band saw and the like. To make the semi circle for the head bed lower part, a cut of the size of a half of a quarter is made where as the core head bed would be size one inch round in shape allowing the core bed to rotate when connecting to the rotating motor. Connecting an electric or manual jack under the core bed head fits the semi circle lubricating to allow smooth ratio of the automatic or manual system. A plywood sheet, plastic sheet, or metal plate can be used to manufacture this innovation. The feet of the core bed has movable wheels to allow the bed to move from one side to another side of room without having to take apart the core bed.

The Main Dialysis Machine may include a bottom to cover the base in order to prevent debris from getting under the front of the wheel of the dialysis machine. The hole in the top of the covering front of the machine is to place gallons of medications which are use in dialysis or pot of flower for decorative purposes. The top base could have other useful purposes. The front covering base is to prevent debris from getting under the wheel. The mirror on top of the machine allows back view of other patients behind you. These parts can be made of a metal plate, plastic or woods, copper and the like. An L shaped holder may be connected to the back mirror and to the back of the dialysis machine. Screws may be used to hold the mirror in place, and the size of the mirror could be any size and length. The material used to mount the mirror may include woods, plastic, metal, copper aluminum and the like.

The present invention may include components for shoulder comfort. This part is to provide a more comfortable hand position allowing hand, neck and shoulder flexibility. The length may be about 12 inches or longer and about 5 ½ inches wide. Materials may include plastic, wood, metal, ceramic clay and the like. These parts can be mounted with screws or glue if desired. The sizes mentioned can be adjusted.

The needle adjuster is used for safety. The purpose of this part is to prevent the needles from dislodging. This part may be about 1 inch in length, about 1 inch wide, and about 1 inch in thick, with a center grove which may be about 5 centimeters in depth and about 5 centimeters in width. The dialysis needles line is put inside the center hole for adjusting the needle position and reducing the likelihood of dialysis needles from coming out of the insertion site, which allows greater blood flow. This part can increase in size or decrease in size. This part can be made with wood, ceramic clay, metal, copper, aluminum, plastic, fabric and the like.

The present invention may include a shower. One main pipe would be connected to the public or commercial water sewer via a pump to draw water into the main pipe. At this point water will be distributed to the main four pipes that are standing vertically and lay horizontally. This system may be used to clean the dialysis machine and also would an ideal part to clean the dialysis chairs. Hot or warm water may be used to perform this procedure. The vertical and horizontal pipes could be aluminum, plastic, iron, copper and the like.

The present invention can be produced by using any appropriate material, which may include metal, wood, plastic, cooper, cotton, cloth, linen, and the like. The present invention can be used by individuals who are dialysis doctor, dialysis nurse, and dialysis technician or a person who is doing home dialysis, emergency room individuals. A method of using the present invention may include the following: apply the blood reducer to a patient with severe bleeding in an emergency room; the doctor may make controlled cuts or punctures with a needle adjuster, which solves the patient's arterial or venous flow. In certain embodiments, other persons at home can use the blood reducer to control bleeding etc.

Doctors perform the operation, the needle adjuster can be use in the medical field, the dialysis bed can be use for specific purpose, which would aid in reducing bed sore because of it specific design. The Global army can use the blood reducer to save a person from bleeding to death. The dialysis bed would improve productivity not just in dialysis setting also in hospital, at private nursing homes or private homes. The present invention reduces the amount of effort it takes to transfer a patient from on bed to another this system is the safest and fastest.

Figure 2:
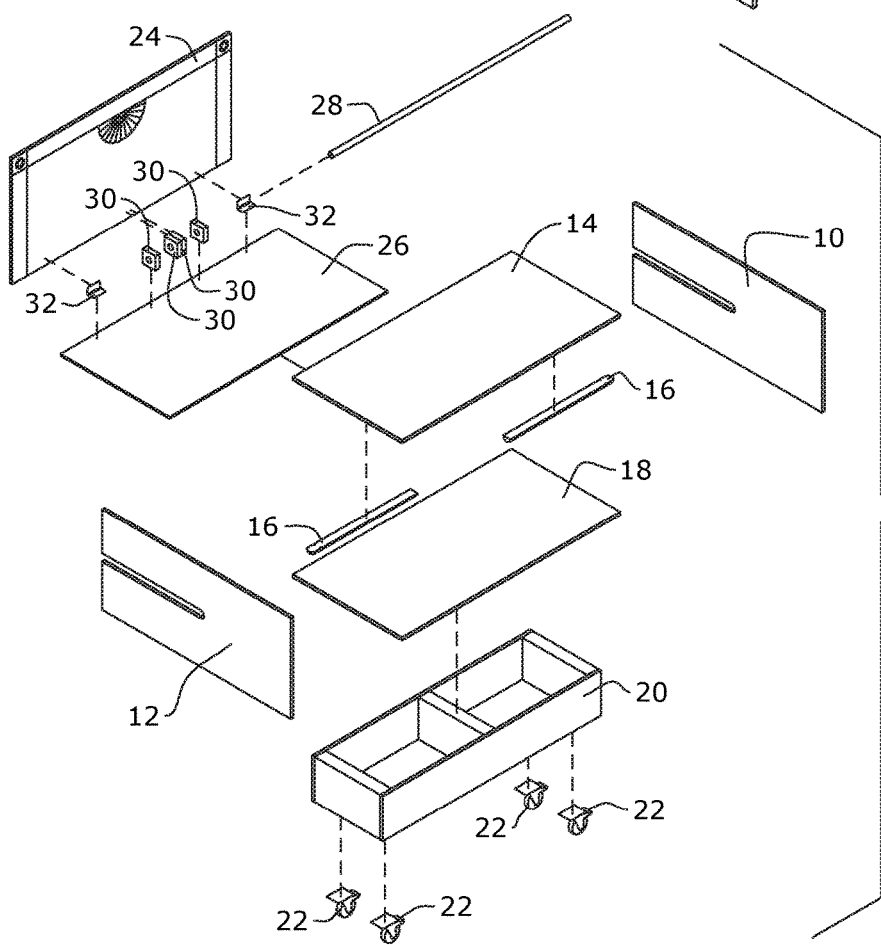
FIG. 2 is an exploded view of the invention.
Figure 3:
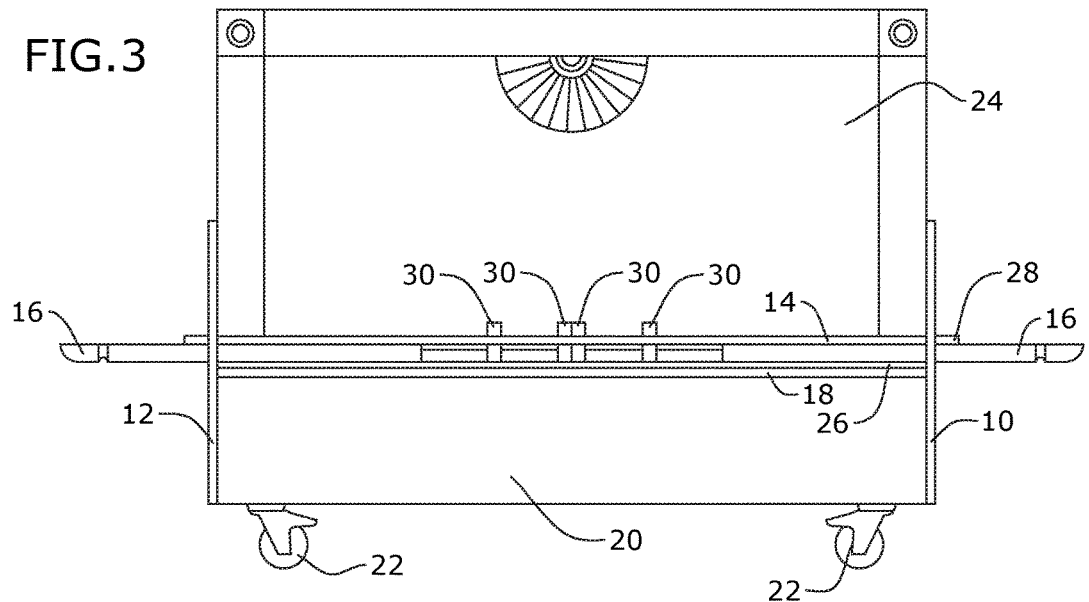
FIG. 3 is a front view of the invention.
Figure 5:
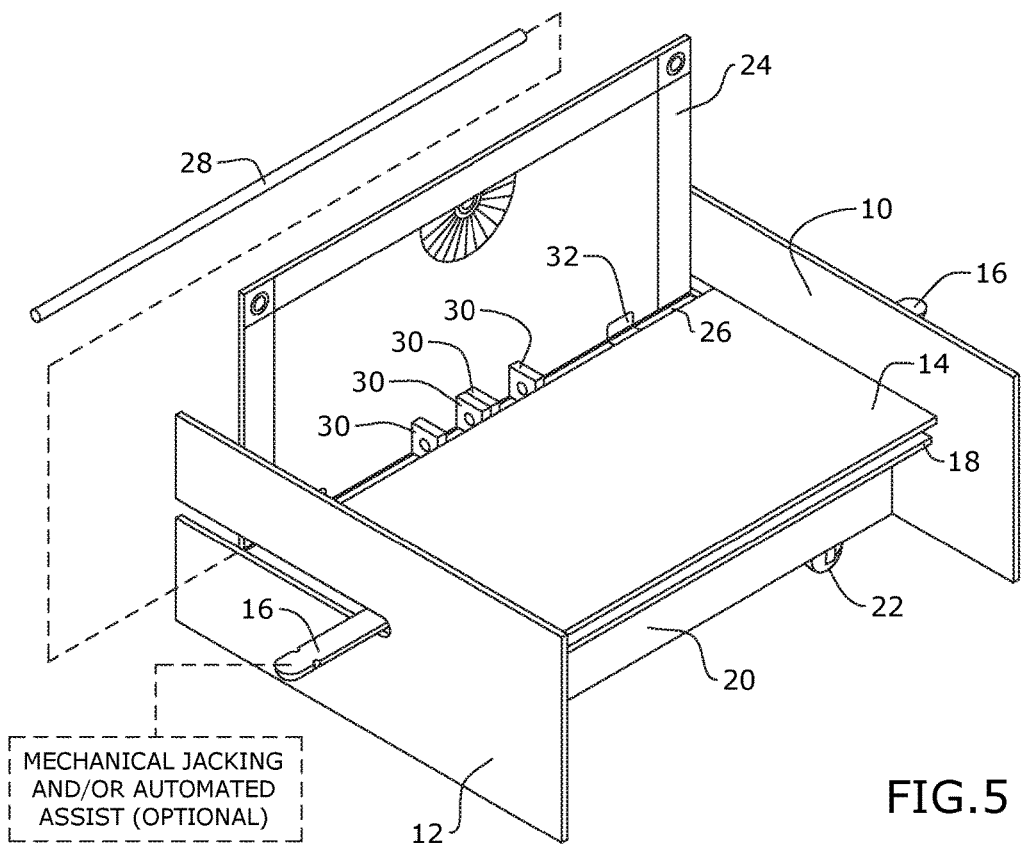
FIG. 5 is a perspective view of the bed illustrating the side panel and side panel base platform being removed.
Figure 8:
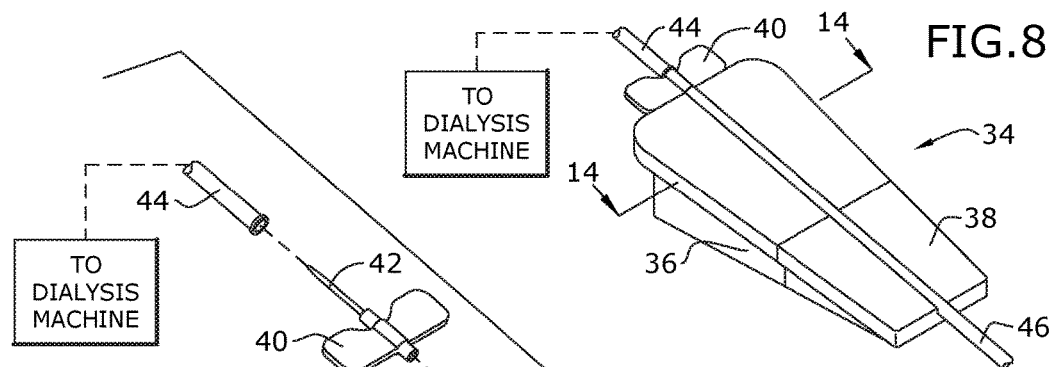
FIG. 8 is a perspective view of the needle adjuster.
Figure 9:
FIG. 9 is an exploded view of the needle adjuster.
Figure 10:
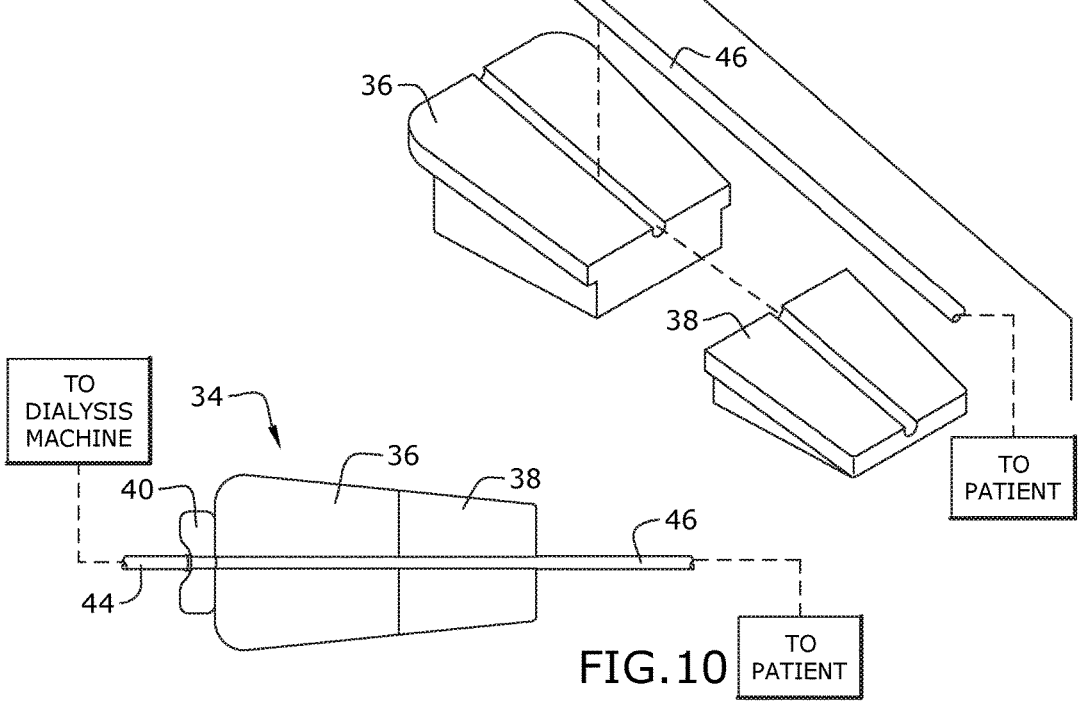
FIG. 10 is a top view of the needle adjuster.
Figure 11:
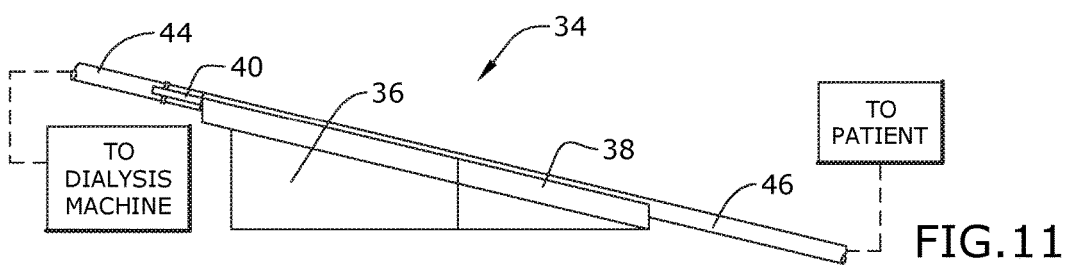
FIG. 11 is a side view of the needle adjuster.
Figure 23:
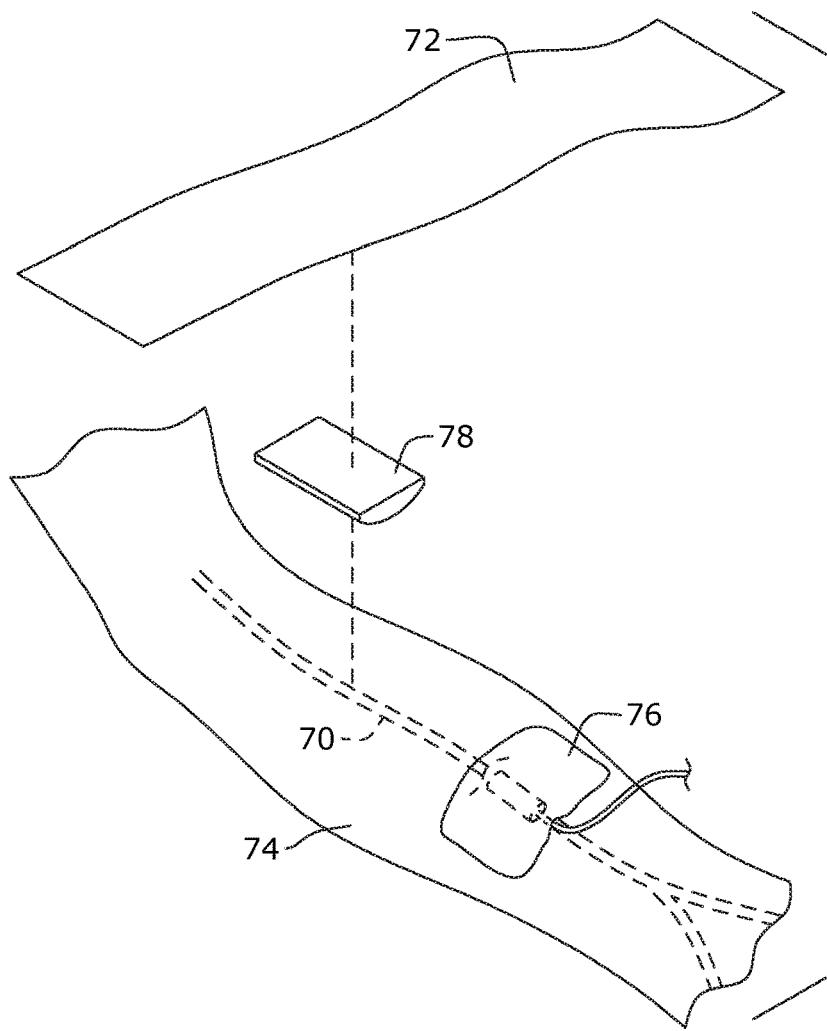
FIG. 23 is an exploded view of a dialysis procedure.
Figure 24:
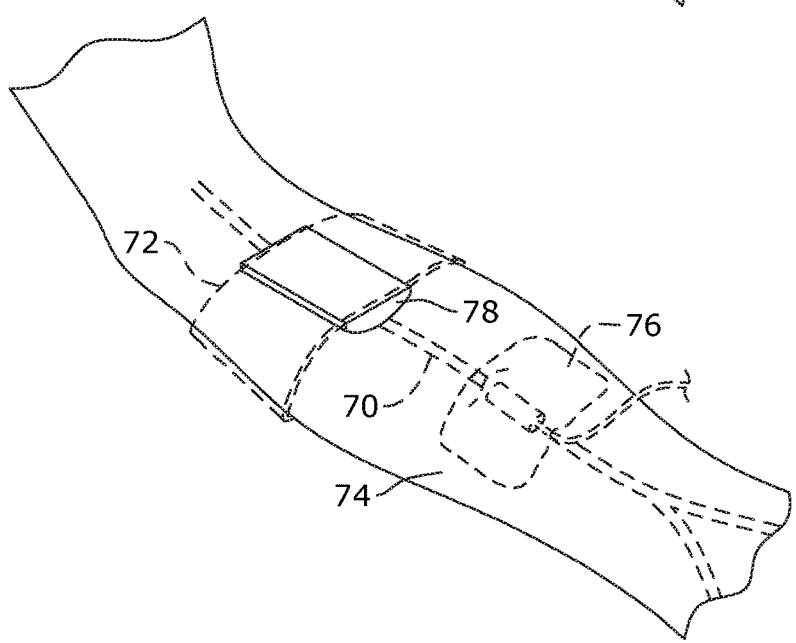
FIG. 24 is a perspective view of a dialysis procedure.

Referring to FIGS. 1 through 24, the present invention includes a dialysis bed and additional accessories. The dialysis bed includes a head board 10, a foot board 12 and a base 20. The head board 10 includes a head board slot 11 running from a side edge towards a central portion of the head board 10. The foot board 12 includes a foot board slot 13 running from a side edge towards a central portion of the foot board 12. The foot board slot 13 aligns with the head board slot 11. The base 20 connects the head board 10 and the foot board 12 together and is disposed beneath the slots 11, 13. The present invention further includes a sliding platform 14. The sliding platform 14 includes a first end having a first handle 16 and a second end having a second handle 16. The first handle 16 slidably engages within the head board slot 11 and the second handle slidably engages within the foot board slot 13.

A user 66 with dialysis may rest on the sliding platform 14 while blood is being exchanged. Due to the handles 16, the sliding platform 14 may move along the slots 11, 13. Therefore, the sliding platform 14 may be adjusted. Further, the user 66 may be transported without leaving the sliding platform 14, since the sliding platform 14 may be removed from the slots 11, 13 and thereby may be removed from the bed.

In certain embodiments, the present invention may further include a stationary platform 18. The stationary platform 18 may be secured to the base 20 and may be disposed below the slots 11, 13. In certain embodiments, the present invention may further include a side barrier 24, 26. The side barrier 24, 26 includes a side panel 24 and a base platform 26 pivotally connected to the side panel 24 by at least one hinge 32, such as two hinges 32. The base platform 26 fits in between the sliding platform 14 and the stationary platform 18.

The side barrier 24, 26 further includes an engaged position and a disengaged position. The engaged position includes the side panel 24 being substantially perpendicular to the base platform 26 and the disengaged position includes the side panel 24 pivoted away from the base platform 26. In such embodiments, the side panel 24 includes at least one hinge pin block 30 having an opening and the base platform 26 includes at least one hinge pin block 30 having an opening that aligns with the opening of the hinge pin block 30 of the side panel 24. A hinge pin 28 fits through the aligned openings of the hinge pin blocks 30, locking the side barrier 24 in the engaged position.

The side barrier 24, 26 may be used for user 66 privacy as well as preventing the sliding platform 14 from being removed. The hinge pin 28 may run through the aligned openings of the hinge pin blocks 30 and the ends of the hinge pin 28 may be disposed within the slots 11, 13 of the head and foot boards 10, 12. When removing the user 66 from the bed via the sliding platform 14, the hinge pin 28 is removed from the aligned openings of the hinge pin blocks 30, allowing the side panel 24 to freely pivot away from the base platform 26. The sliding panel 14 may then be adjusted or removed from the bed.

The dialysis bed of the present invention may also be mobile. For example, a plurality of wheels may be secured to a bottom of the base 20. The plurality of wheels may be a plurality casters 22. In certain embodiments, the present invention may include four casters 22, one at each corner of the bottom of the base 20. Therefore, the user 66 may be transported without interrupting the dialysis process.

The present invention may further include an armrest 48. The armrest 48 may elevate the user's arm during the blood exchange. The armrest 48 may be disposed on the top surface of the sliding platform 14.

The present invention may include a needle guide 34 disposed on a top surface of the sliding platform 14. The needle guide 34 may include an upper block 36 having an angled top surface and an upper block channel formed on the angled top surface. The needle guide 34 may further include a lower block 38 having an angled top surface and a lower block channel formed on the angled top surface. The upper block 36 and the lower block 38 are disposed together so that the angled top surface of the upper block 36 aligns with the angled top surface of the lower block 38 and the upper block channel aligns with the lower block channel forming a single channel sized to retain a tube 46 within. The tube 46 may be secured to a butterfly clamp 40 having a needle 42. The needle 42 may fit within a second tube 44 running to the dialysis machine.

The dialysis may take place using a blood reducer 78 secured to the forearm 74 by surgical tape 72. The needle may be inserted into the forearm 74 at a port location 76 to exchange blood from the vein 70. A certain type of pants 50 may be used with the present invention. In such embodiments, the pants 50 may include flaps disposed around a knee area. The flaps may be openable and closeable via zippers 52, providing easy access for tubing to run to the user 66.

The present invention may further include a cleaning system 54. The cleaning system 54 may include a shower. The cleaning system 54 may be used to clean a dialysis machine 60. The dialysis machine 60 may be supported by first supports 62 and second supports 64. The dialysis machine 60 may include a prescription tray 56 having cup holders to hold prescription cups 58. The cleaning system 54 delivers water 68 to the dialysis machine 60.

It should be understood, of course, that the foregoing relates to exemplary embodiments of the invention and that modifications may be made without departing from the spirit and scope of the invention as set forth in the following claims.

What is claimed is:

1. A dialysis bed comprising:
    a head board comprising a head board slot running from a side edge towards a central portion of the head board;
    a foot board comprising a foot board slot running from a side edge towards a central portion of the foot board, wherein the foot board slot aligns with the head board slot;
    a base connecting the head board and the foot board together; and
    a sliding platform comprising a first end comprising a first handle and a second end comprising a second handle, wherein the first handle slidably engages within the head board slot and the second handle slidably engages within the foot board slot.

2. The dialysis bed of claim 1, further comprising a stationary platform secured to the base and disposed below the head board slot and the foot board slot.

3. The dialysis bed of claim 2, further comprising a side barrier, wherein the side barrier comprises a side panel and a base platform pivotally connected to the side panel by at least one hinge, wherein the base platform fits in between the sliding platform and the stationary platform.

4. The dialysis bed of claim 3, wherein the side barrier further comprises an engaged position wherein the side panel is substantially perpendicular to the base platform and a disengaged position wherein the side panel is pivoted away from the base platform.

5. The dialysis bed of claim 4, wherein the side panel comprises at least one hinge pin block comprising an opening, wherein the base platform comprises at least one hinge pin block comprising an opening that aligns with the opening of the hinge pin block of the side panel, wherein a hinge pin fits through the aligned openings locking the side barrier in the engaged position.

6. The dialysis bed of claim 1, further comprising a plurality of casters secured to a bottom of the base.

7. The dialysis bed of claim 1, further comprising an armrest disposed on a top surface of the sliding platform and operable to elevate a user's arm.

8. The dialysis bed of claim 1, further comprising a needle guide disposed on a top surface of the sliding platform.

9. The dialysis bed of claim 8, wherein the need guide comprises:
    an upper block comprising an angled top surface and an upper block channel formed on the angled top surface;
    a lower block comprising an angled top surface and a lower block channel formed on the angled top surface, wherein
    the angled top surface of the upper block aligns with the angled top surface of the lower block,
    the upper block channel aligns with the lower block channel forming a single channel sized to retain a tube within.

* * * * *